United States Patent [19]

Reategui et al.

[11] Patent Number: 4,950,893

[45] Date of Patent: Aug. 21, 1990

[54] METHOD AND APPARATUS FOR ENHANCED ION SPECTRA GENERATION AND DETECTION IN ION MOBILITY SPECTROMETRY

[75] Inventors: Julio A. Reategui, Hunt Valley; Glenn E. Spangler, Lutherville; Joseph L. Mangum, Baltimore, all of Md.

[73] Assignee: Environmental Technologies Group, Inc., Baltimore, Md.

[21] Appl. No.: 344,128

[22] Filed: Apr. 27, 1989

[51] Int. Cl.⁵ .......................................... H01J 49/40
[52] U.S. Cl. ...................................... 250/282; 250/287
[58] Field of Search ................... 250/287, 282; 422/98

[56] References Cited

U.S. PATENT DOCUMENTS 3,626,182 12/1971 Cohen .................................. 250/287
4,633,083 12/1986 Knorr et al. ........................ 250/287

Primary Examiner—Jack I. Berman
Attorney, Agent, or Firm—Leonard Bloom

[57] ABSTRACT

A method for operating an Ion Mobility Spectrometer in which an analyte sample is ionized in the spectrometer reaction chamber and the analyte ions are permitted to flow freely from the reaction chamber into the spectrometer drift chamber. The ion current output from the spectrometer ion current detector is observed during this time. The ion flow from the reaction chamber to the drift chamber is then momentarily interrupted and the time delay between the time of ion flow interruption and the appearance of a decrease in the ion current detector output is observed. Different substances are characterized by different delays. The concentrations of the different substances may be determined by measuring the change in detected ion current after the ion flow interruption.

8 Claims, 3 Drawing Sheets

METHOD AND APPARATUS FOR ENHANCED ION SPECTRA GENERATION AND DETECTION IN ION MOBILITY SPECTROMETRY

FIELD OF THE INVENTION

The present invention relates to ion mobility spectrometry (IMS). More particularly, it relates to a novel method of operating ion mobility spectrometer apparatus of known construction. The method of the invention is distinguished from prior operating methods by reversing the function of the shutter grid, a common feature of IMS apparatus. In accordance with the invention, the shutter grid is normally biased open to admit ions to the drift region of the IMS cell and then briefly biased closed to establish distinct incremental volumes which are void of ions and which transit the IMS cell with velocities which are characteristic of the constituent substances of the analyte present in the IMS cell.

BACKGROUND OF THE INVENTION

Ion mobility spectrometry (IMS) is an accepted analytical method for determining the identity and concentration of trace substances present in an analyte. The basic apparatus used in the IMS process comprises an analyzer cell, a power supply furnishing accelerating and control voltages to the cell, means for ionizing samples of analyte admitted to the cell and means for determining the times required for the ions of the various substances present in the cell to traverse a specific length of the cell under the influence of an accelerating electric field and against the force of a stream of an inert drift gas flowing through the cell in the direction opposite to that of the electric field.

U.S. Pat. No. 4,633,083, issued Dec. 30, 1986, describes an Ion Mobility Spectrometer in greater detail and sets forth several conventional methods for operating the apparatus, as well as the method which is unique to the patent. The first of these methods is denominated the single scan method in which the ion entrance gate is opened for a brief period to admit a pulse of ions to the cell drift region. The small ion cloud progresses through the drift region and is separated thereby into constituent ion groups which arrive at the ion detector at different times according to the differences in mass, size and charge of the molecules of each of the groups of the constituents. Observation of the arrival times of the groups at the detector enable the identification of the molecules making up a group and measurement of the ion current resulting from the impingement of a group on the detector permits determination of the concentrations of the substances.

Another method described in the referenced patent is termed the moving second gate method. The analyzer cell used in this method includes a second ion gate, the exit gate, positioned adjacent the ion detector. The exit gate is selectively opened for a short period, usually equal to the open period of the entrance gate, to permit detection of the ions located in the near vicinity of the exit gate at the opening time. The opening of the exit gate is delayed from the opening of the entrance gate an amount of time corresponding to the time required for the ions of a particular substance to transit the cell drift region. Thus, only the ions of a particular substance will be detected for each specific delay time. By scanning the delay times, a spectrum of the substances present in the analyte may be developed.

The method of the referenced patent involves apparatus in which the analyzer cell is provided with both an ion entrance gate and an ion exit gate. Instead of delaying the opening of the exit gate from the opening of the entrance gate, as in the moving second gate method, the entrance gate and the exit gate are opened and closed simultaneously at relatively high frequencies. Such method enables the selective detection of molecules having transit times which are in phase with the gate operating frequency.

SUMMARY OF THE INVENTION

All of the above-described operating methods of the prior art have one feature in common. Namely, that the bulk of the ions generated in the analyzer cell reaction region are excluded from entering the analyzer cell drift region, or if present in the analyzer cell drift region, the bulk of the ions therein are excluded from detection.

In accordance with the method of the present invention, the function of the ion entrance gate of the prior analyzer cells is reversed, so that now the gate is normally biased open to admit ions from the cell reaction region to the cell drift region for the major portion of the time. Ions entering the drift region traverse the drift region and are detected to generate a baseline ion current of a steady, relatively high level. Then the ion entrance gate is biased closed for a brief interval, corresponding to the gate open interval of the prior art, to create an incremental volume in the cell drift region which is void of ions. The void transits the cell drift region, separating in the course thereof into constituent voids having transit times and volumes corresponding to those of the ion populated pulses of the constituents of the prior art. Significant advantages of method of the invention include a substantial improvement in signal to noise ratio as compared to the prior art methods operating under similar conditions; improved signal pulse shape and width as compared to prior art methods under similar conditions; and, the enablement of measurement of the total cell ion current on a continuous basis, thereby permitting a more precise determination of the concentration of the constituents of an analyte.

Accordingly, it is an object of the present invention to provide a method of operating Ion Mobility Spectrometry apparatus having improved sensitivity for the detection of the constituent substances of an analyte which are low in concentration.

It is another object of the invention to provide a method of operating Ion Mobility Spectrometry apparatus providing improved resolution of the waveforms of the output signals from such apparatus to enable more accurate determinations of the identities and concentrations of the constituent substances of an analyte.

Still another object of the invention is to provide a method of operating Ion Mobility Spectrometry apparatus which permits the measurement of total ion current on a continuous basis, thereby eliminating periodic interruptions in service of the apparatus for calibration purposes and permitting more accurate determinations of the concentrations of the constituent substances of an analyte.

DETAILED DESCRIPTION OF THE INVENTION

Figure 1:
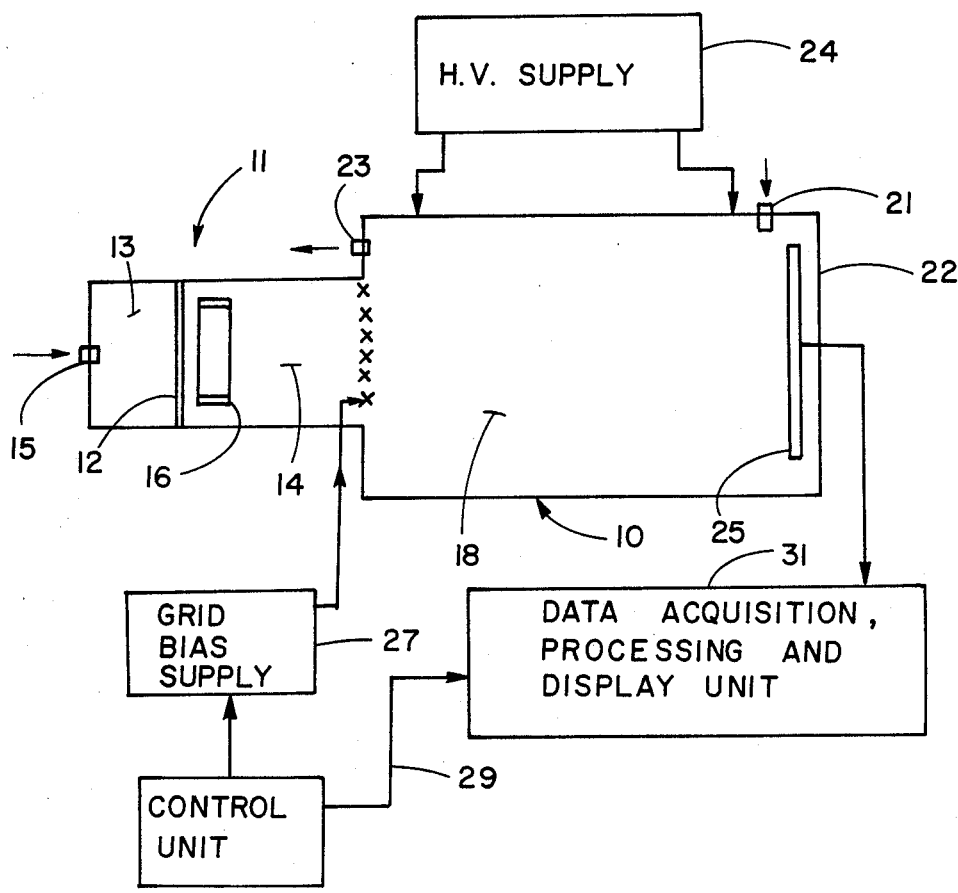
FIG. 1 is a functional block diagram of an Ion Mobility Spectrometer.

FIG. 1 is a simplified block diagram of a typical Ion Mobility Spectrometer used in the practice of the method of the invention. The spectrometer comprises an analyzer cell 10 of generally cylindrical form, closed at both ends. The forward end 11 of the cell may be divided by a permselective membrane 12 into a sample chamber 13 and a reaction region 14. An analyte sample is admitted to the sample chamber through an inlet 15, often being transported therethrough by a carrier gas. The molecules of the analyte sample selectively diffuse through the membrane into the reaction region 14. There the analyte molecules mix with a reactant gas or vapor present in the region to form readily ionizable product molecules. These product molecules are ionized by the emissions of an ionizing source 16, suitably a ring of radioactive Ni63. The reaction region of the cell is divided from the drift region 18 of the cell by a shutter grid 17. A steady stream of inert drift gas is flowed through the drift region 14 from an inlet 21, located near the end 22 of the cell, toward a vent 23, located near the shutter grid 17 at the inlet to the drift region.

A high voltage supply 24 provides an static electric field which is distributed uniformly within the cell along the length of the drift region 18 and which is polarized oppositely to the ions generated within reaction region 14 so as to accelerate ions escaping from the reaction region through the drift region towards the end 22 of the cell. An electrometer 25 or other suitable ion current detector is positioned near the end 22 of the cell to detect the ion currents and the arrival times of the ions traversing the drift region of the cell.

A control circuit controls the operation of a shutter grid bias supply 27 and supplies a synchronizing signal on line 29 to a data acquisition, processing and display unit 31 marking the start of a time base generated therein against which the appearance of ion currents from detector 25 is marked. Unit 31 may include means for converting the current outputs of detector 25 to digital form, for storing and processing such signal outputs to enhance the information content and for telemetering or displaying the information in various forms in accordance with known algorithms and processes.

As taught by the methods of the prior art, grid bias supply 27 is pulsed for a brief interval to supply a momentary bias pulse to shutter grid 17, otherwise known as the ion entrance gate, which is of an attractive polarity to the ions in the reaction region 14 of the cell, thereby admitting a small pulse of ions to the cell drift region 18. At all other times bias supply 27 furnishes a bias voltage to shutter grid 17 which is of repellant polarity to the ions in the reaction region 14 thereby closing off the drift region 18 of the cell from the admission of ions for the major portion of the data acquisition time of the system.

In the method of the present invention the polarities of the bias voltages applied to shutter grid 17 by bias supply 27 are reversed from those applied in the methods of the prior art so that instead of applying a momentary bias pulse to the shutter grid of polarity attractive to the ions in the reaction region a momentary bias pulse of repellant polarity is applied, and instead of maintaining the shutter grid biased with a potential which is repellant to the ions of the reaction region for the major portion of the data acquisition time, the shutter grid is biased with a potential which is of an attractive polarity or, at least, passive, permitting the free flow of ions from the reaction region into the drift region for the major portion of the data acquisition time. Then, instead of admitting a short pulse ions into the cell drift region, a short void is created in the otherwise free flowing ion stream in the cell drift region. This void transits the drift region of the cell and is separated in the course thereof into smaller voids having arrival times at the cell detector which correspond to the arrival times of the constituent ion groups generated by prior methods and creating gaps in the otherwise steady output current of the detector having waveforms which are better defined and have better signal/noise ratios than do the signal waveforms produced by prior methods. The improvements afforded by the present invention are evidenced by the representations of oscilloscope displays contained in FIGS. 2-6, which were obtained during tests comparing the method of the present invention with a frequently used method of the prior art.

Figure 2:
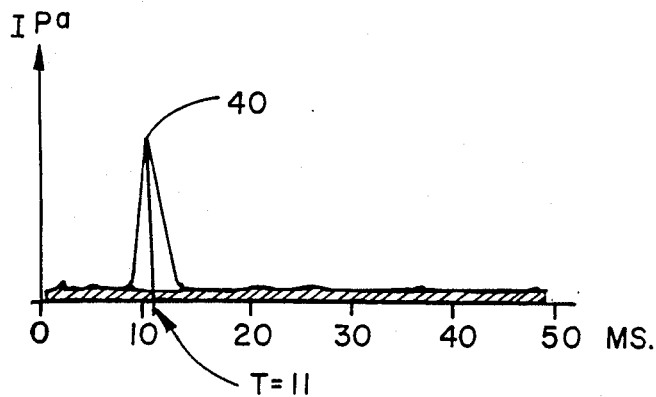
FIG. 2 is a representation of an oscilloscope display of the detected ion current when an IMS is operated in accordance with a frequently used method of the prior art.

FIG. 2 shows the oscilloscope display of signal current obtained from an IMS when a test substance is applied and the shutter grid is biased open for an interval of 0.8 milliseconds during a total scan time of 50 milliseconds. The shutter grid is biased open at t=0 and biased closed at t=0.8 milliseconds. The resultant ion current peak 40 appears at the detector at approximately t=11 milliseconds and the ion current waveform is approximately 6 milliseconds wide at the base. The measured signal/noise ratio is approximately 30:1.

Figure 3:
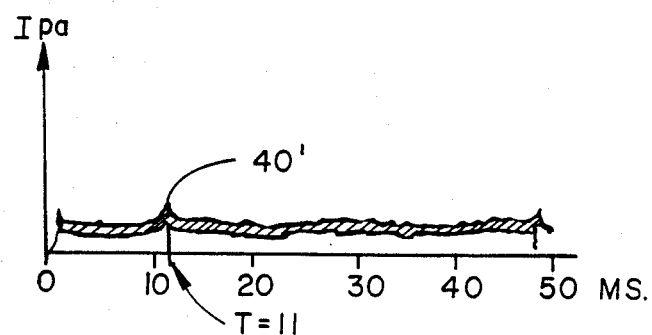
FIG. 3 is a representation of an oscilloscope display of the detected ion current from an IMS operated in the same manner and under the same conditions as those of FIG. 1 except that the time interval during which the shutter grid is biased open has been reduced by one-half.

FIG. 3 shows the ion current detected under the same conditions as those of FIG. 2, except that the shutter grid is biased open only for an interval of 0.4 milliseconds. The peak ion current 40' is barely discernable even though the oscilloscope vertical gain has been increased by 2.5 times. The measured signal/noise ratio is this case is approximately 2.7:1.

Figure 4:
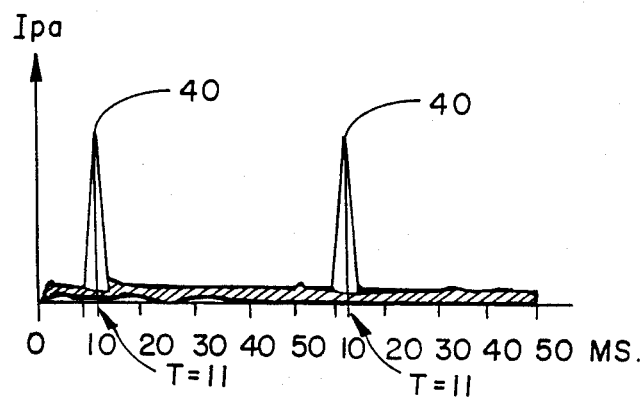
FIG. 4 is a representation of an oscilloscope display obtained under the same conditions as those in FIG. 1 showing a double scan presentation of the detected ion current.

FIG. 4 is a representation of an oscilloscope display of the ion current detected from an IMS operated in the same manner and under the same conditions as those of FIG. 2 except that here the results of two consecutive scans or operating cycles are presented. The time scale of the display is necessarily compressed, but otherwise the ion current waveforms are similar to those of FIG. 2.

Figure 5:
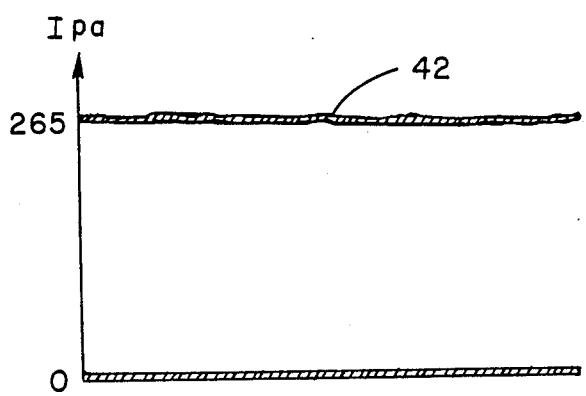
FIG. 5 is a representation of an oscilloscope display of the total ion current detected from an IMS when the shutter grid thereof is biased open continuously.

FIG. 5 is a representation of an oscilloscope display obtained from an IMS when the same test substance and concentration thereof is applied to the IMS as was used in obtaining FIG. 3 and when the shutter grid is biased continuously open. The total ion current 42 appears on the screen as a steady line forming an accurate reference against which peak deflections may be measured.

Figure 6:
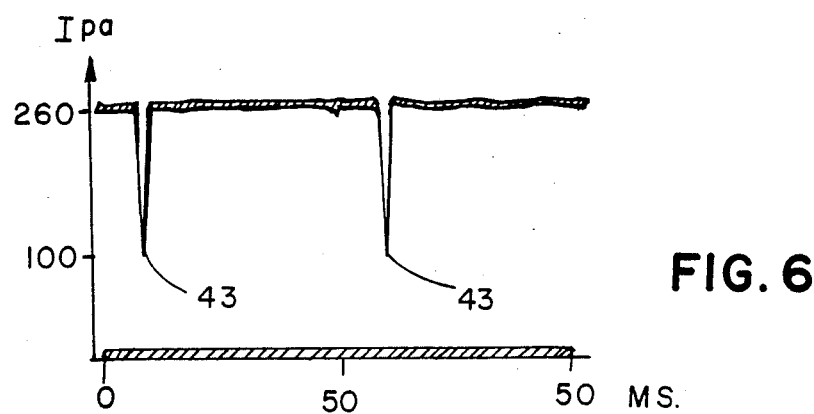
FIG. 6 is a representation of an oscilloscope display of the ion current detected from an IMS operated in accordance with the method of the present invention using the same test substance and concentration thereof as was used to obtain FIGS. 2-4.

FIG. 6 is a representation of an oscilloscope display of the ion current from an IMS operated in accordance with the method of the invention. The test substance and concentration used in obtaining FIG. 6 was the same as that used in obtaining FIGS. 2-4. In the present method, the shutter grid is normally biased open to permit the free flow of ions from the reaction region of the analyzer cell to the drift region of the cell. At $t=0$ the shutter grid is biased closed for an interval of 0.4 milliseconds and then immediately biased open for the remainder of the scan. The void in ion current created by the closed shutter grid progresses through the drift region of the cell and appears at the detector as a sharp, well-defined gap 43 in ion current at approximately $t=10$.

Comparing FIG. 4 with FIG. 6, note that gap 43 retains a sharp, narrow shape, being broadened only slightly in transiting the cell drift region. The ion current waveform of FIG. 4, originally 0.8 milliseconds wide, becomes broadened to approximately 6 milliseconds width in the same course. The broadening of the ion current pulse in FIG. 4 is due largely to the mutually repellant Coulomb forces of the ions contained in the pulse, tending to expand and disperse the ion group.

In the case of FIG. 6, however, the ions bound the void 43 and the same Coulomb forces tending to expand the pulse of FIG. 4 now tend to compress the shape of the void 43. The improved signal waveforms obtained by practice of the present invention provide increased resolution in the signal waveforms for better identification of the substances contained in an analyte.

Note also that the gate closed interval of 0.4 milliseconds used in obtaining FIG. 6 is to be compared to the gate open interval of 0.4 milliseconds used in obtaining FIG. 3, which provided barely usable data. It is to be expected, therefore, that the method of the invention will provide not only improved resolution but improved signal/noise ratio, as well.

A theoretical foundation for the method of the invention may be developed from the mathematical theory describing the conventionally operated IMS as published by G. E. Spangler and C. I. Collins, Analytical Chemistry 47, 403 (1975).

Obviously, the data obtained by practice of the invention may be processed, stored and displayed in the same manner as the data obtained by practice of conventional methods. The invention is applicable to multiple scan and other signal averaging techniques, and affords the advantage of providing a continuous measurement of total ion current to serve as a reference for calibration purposes.

The invention claimed is:

1. A method for operating ion mobility spectrometry apparatus, said apparatus including:

an analyzer cell having a shutter grid for dividing said cell into a reaction region and a drift region;

means for introducing an analyte sample into said cell reaction region;

means in said cell reaction region for ionizing molecules of said analyte sample present therein;

means for establishing an electric field extending along the length of said drift region of said cell in a direction away from said reaction region of said cell;

means for establishing a flow of drift gas through said drift region of said cell in a direction opposite to the direction of said electric field;

an ion current detector, said detector being positioned in said drift region of said cell near the end of said drift region opposite said reaction region of said cell; and means for supplying a bias potential to said shutter grid, the polarity of said bias potential being selectable to either permit the free flow of ions from said cell reaction region to said cell drift region or to prevent the free flow of ions from said cell reaction region to said cell drift region;

said operating method comprising the steps of:

selecting first the polarity of bias potential output from said supply means which permits the free flow of ions from said cell reaction region to said cell drift region;

applying said first selected polarity of bias potential to said shutter grid;

selecting second that said bias potential polarity which prevents the free flow of ions from cell reaction region to said cell drift region;

momentarily applying said second selected polarity of bias potential to said shutter grid to interrupt the flow of ions from said cell reaction region to said cell drift region;

restoring the application of said first selected polarity of bias potential to said shutter grid immediately after said momentary application thereto of said second selected polarity of bias potential;

observing the ion current produced by said ion current detector;

observing the elapsed time between the application of said second selected polarity of bias potential to said shutter grid and the occurrence of a reduction in ion current from said ion detector.

2. The method as claimed in claim 1, with the additional step of:

observing the ion current produced by said ion current detector during the application of said first selected polarity of bias potential to said shutter grid.

3. The method as claimed in claim 1, with the additional step of:

observing the amount of reduction in ion current occurring after said application of said second selected polarity of bias potential to said shutter grid.

4. The method as claimed in claim 1 wherein;

said second selected polarity is applied to said shutter grid for a interval of between 0.2 and 0.4 milliseconds in duration.

5. The method as claimed in claim 4 wherein:

said step of observing the ion current produced by said ion current detector continues through a period beginning at least at the time of said application of said second selected polarity of bias to said shutter grid and extending until about 50 milliseconds thereafter.

6. A method for analyzing a chemical sample utilizing an Ion Mobility Spectrometer, said spectrometer including:

a reaction chamber having means for ionizing sample substances introduced therein, a drift chamber with means for subjecting ions therein to the forward propelling force of an electric field against the retarding flow of an inert gas, a controllable shutter grid for either permitting or prohibiting the flow of ions from the reaction chamber to the drift chamber and a means for detecting ion currents generated by ions traversing the drift chamber against the retarding flow of gas, said method comprising:

introducing a sample to be analyzed to said reaction chamber;

controlling said shutter grid so as to permit the free flow of ions from said reaction chamber to said drift chamber;

observing the output of said ion current detector means;

controlling said shutter grid so as to momentarily prohibit the flow of ions from said reaction chamber to said drift chamber; and observing the time delay occurring between said momentary prohibition of ion flow and the appearance of a decrease in the output of said ion current detector means.

7. The method as claimed in claim 6, with the additional step of:

observing the magnitude of the decrease in the output of said ion current detector means after said momentary prohibition of ion flow.

8. The method as claimed in claim 7 wherein:

said step of momentarily prohibiting ion flow is effective to prohibit ion flow for a period of from about 0.2 to 1.0 milliseconds in duration.

* * * * *